(12) United States Patent
Fukunaka et al.

(10) Patent No.: US 9,577,124 B2
(45) Date of Patent: Feb. 21, 2017

(54) INFRARED SENSOR AND METHOD FOR MANUFACTURING SAME, FILTER MEMBER FOR INFRARED SENSOR, AND PHOTOCOUPLER

(71) Applicant: ASAHI KASEI MICRODEVICES CORPORATION, Tokyo (JP)

(72) Inventors: Toshiaki Fukunaka, Tokyo (JP); Yasutaka Myoraku, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

(21) Appl. No.: 14/647,920

(22) PCT Filed: Nov. 29, 2013

(86) PCT No.: PCT/JP2013/007022
§ 371 (c)(1),
(2) Date: May 28, 2015

(87) PCT Pub. No.: WO2014/087619
PCT Pub. Date: Jun. 12, 2014

(65) Prior Publication Data
US 2015/0303321 A1    Oct. 22, 2015

(30) Foreign Application Priority Data
Dec. 5, 2012  (JP) .................................. 2012-266203

(51) Int. Cl.
*G01J 5/00* (2006.01)
*H01L 31/0232* (2014.01)
(Continued)

(52) U.S. Cl.
CPC ............ *H01L 31/02327* (2013.01); *G01J 1/02* (2013.01); *G01J 1/0271* (2013.01); *G01J 1/04* (2013.01);
(Continued)

(58) Field of Classification Search
CPC ...... G01N 21/2504; G01N 21/35; G01N 21/61
(Continued)

(56) References Cited

U.S. PATENT DOCUMENTS

2011/0090505 A1*  4/2011  Kuze .................. G01N 21/3504
356/437

FOREIGN PATENT DOCUMENTS

JP     2006-194691 A     7/2006
JP     2010-133946 A     6/2010
(Continued)

OTHER PUBLICATIONS

Extended European Search Report dated Jul. 8, 2016 in corresponding European Patent Application No. 13859737.2.
(Continued)

*Primary Examiner* — David Porta
*Assistant Examiner* — Meenakshi Sahu
(74) *Attorney, Agent, or Firm* — Morgan, Lewis & Bockius LLP

(57) ABSTRACT

A filter member includes a first lead terminal, an optical filter, and a first mold member, and a light incidence surface and a light emission surface of the optical filter is exposed from the first mold member. A sensor member includes an IR sensor element, a second lead terminal and a second mold member. A light-receiving surface of the IR sensor element is exposed from the second mole member. The filter member is disposed on the sensor member so that the light emission surface of the optical filter faces the light-receiving surface of the IR sensor element in the sensor member.

25 Claims, 12 Drawing Sheets

(51) Int. Cl.

| | |
|---|---|
| *G01N 21/3504* | (2014.01) |
| *H01L 31/173* | (2006.01) |
| *G01J 1/02* | (2006.01) |
| *G01J 1/04* | (2006.01) |
| *G01N 21/35* | (2014.01) |
| *G01N 21/61* | (2006.01) |
| *H01L 31/02* | (2006.01) |
| *H01L 31/12* | (2006.01) |
| *G02B 5/20* | (2006.01) |
| *H01L 31/09* | (2006.01) |
| *H01L 31/16* | (2006.01) |

(52) U.S. Cl.
CPC ............ *G01J 1/0492* (2013.01); *G01N 21/35* (2013.01); *G01N 21/3504* (2013.01); *G01N 21/61* (2013.01); *G02B 5/208* (2013.01); *H01L 31/02* (2013.01); *H01L 31/0232* (2013.01); *H01L 31/02325* (2013.01); *H01L 31/09* (2013.01); *H01L 31/12* (2013.01); *H01L 31/16* (2013.01); *H01L 31/173* (2013.01)

(58) Field of Classification Search
USPC ...................................................... 250/338.1
See application file for complete search history.

(56) References Cited

FOREIGN PATENT DOCUMENTS

| | | |
|---|---|---|
| JP | 2011-080772 A | 4/2011 |
| JP | 2012-112728 A | 6/2012 |
| JP | 2012-199311 A | 10/2012 |
| JP | 2012-215445 A | 11/2012 |

OTHER PUBLICATIONS

International Search Report dated Mar. 4, 2014, for International application No. PCT/JP2013/007022.
International Preliminary Report on Patentability dated Jun. 9, 2015, for corresponding International application No. PCT/JP2013/007022.

\* cited by examiner

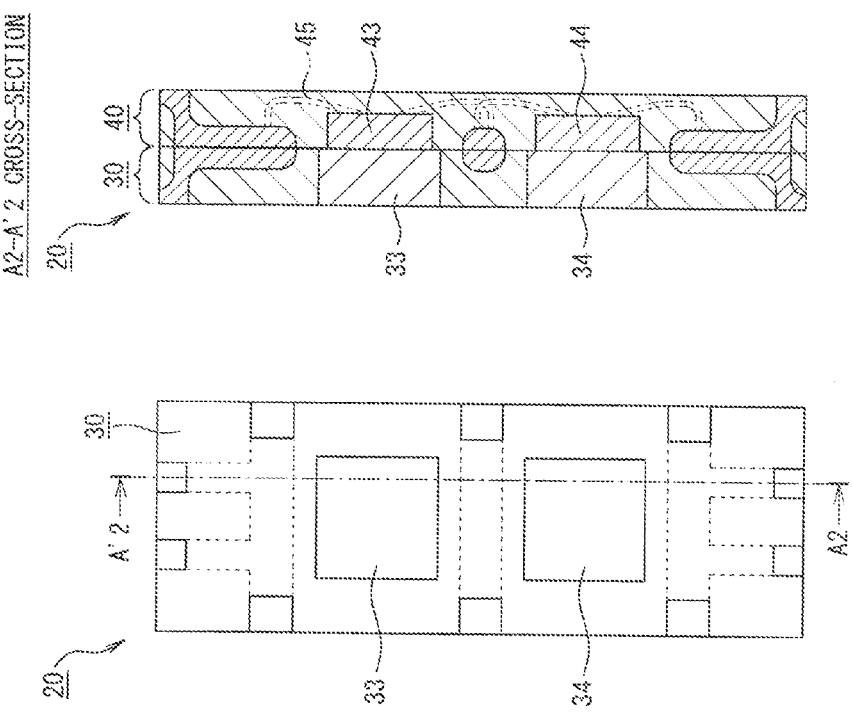
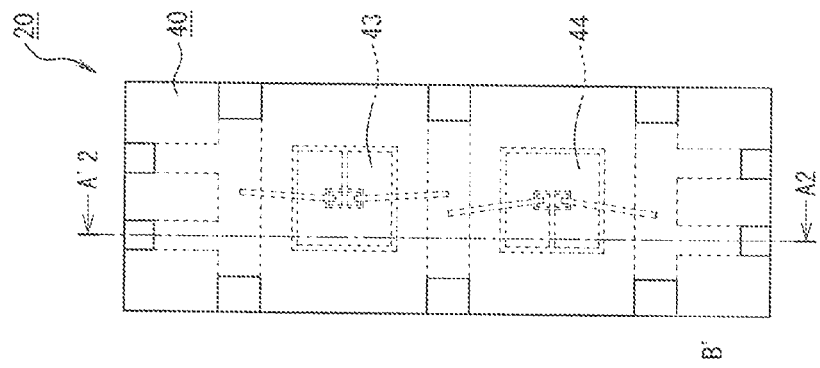

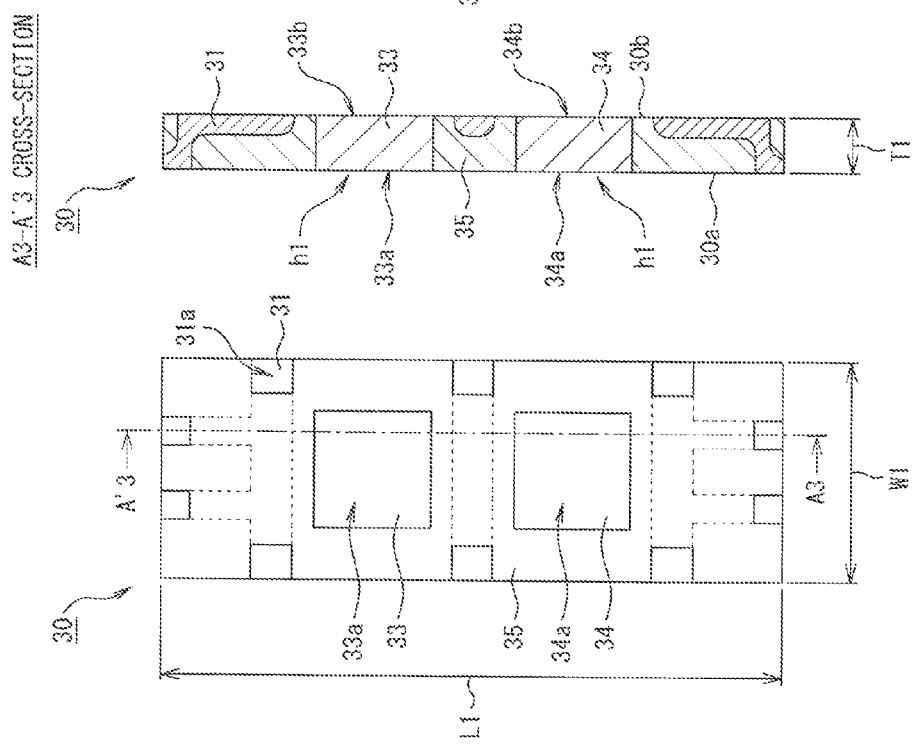

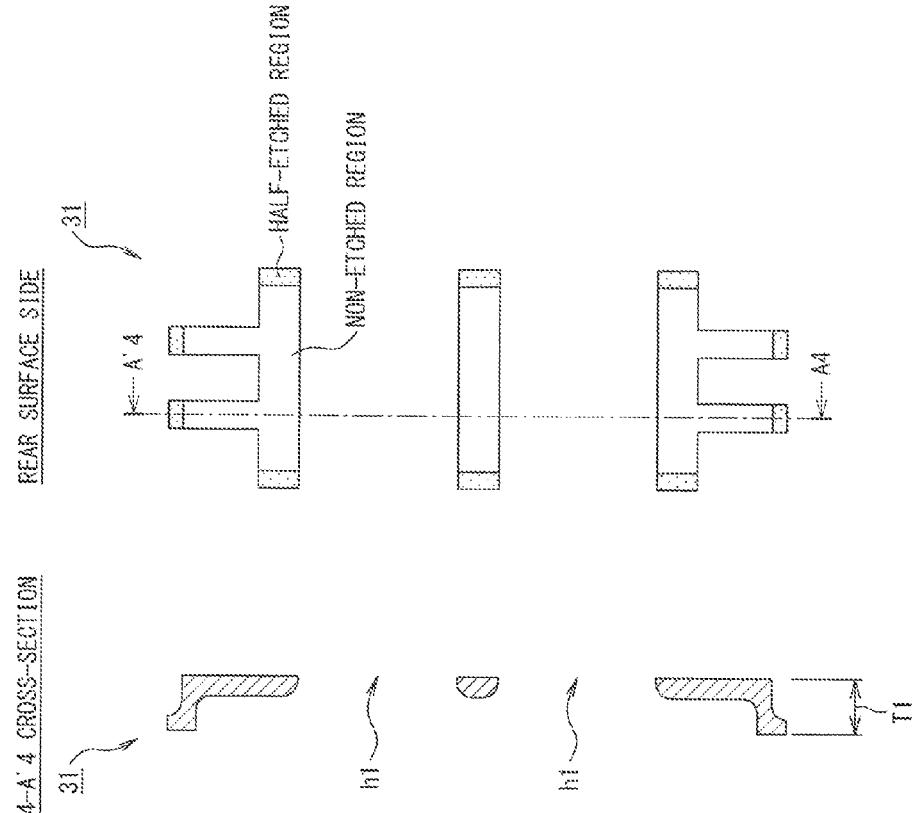
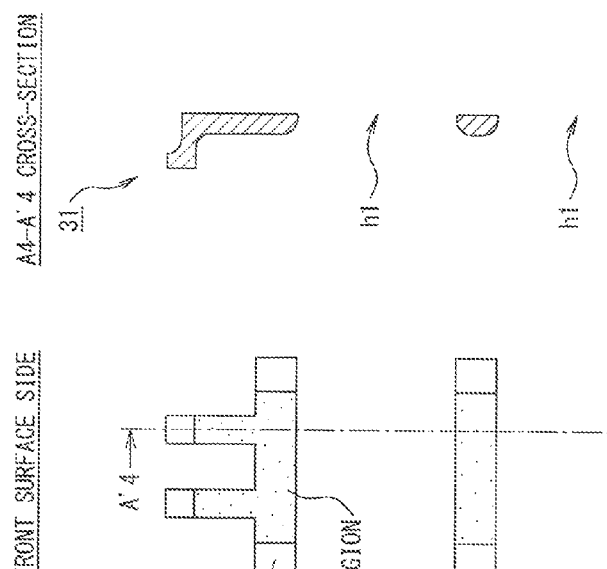
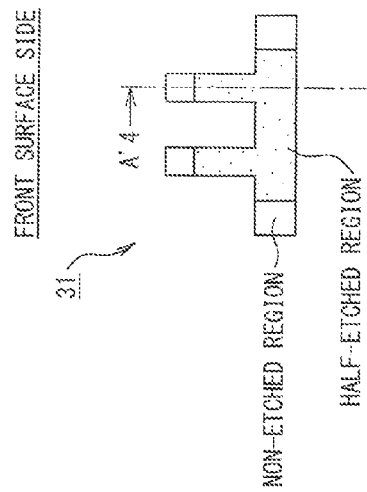

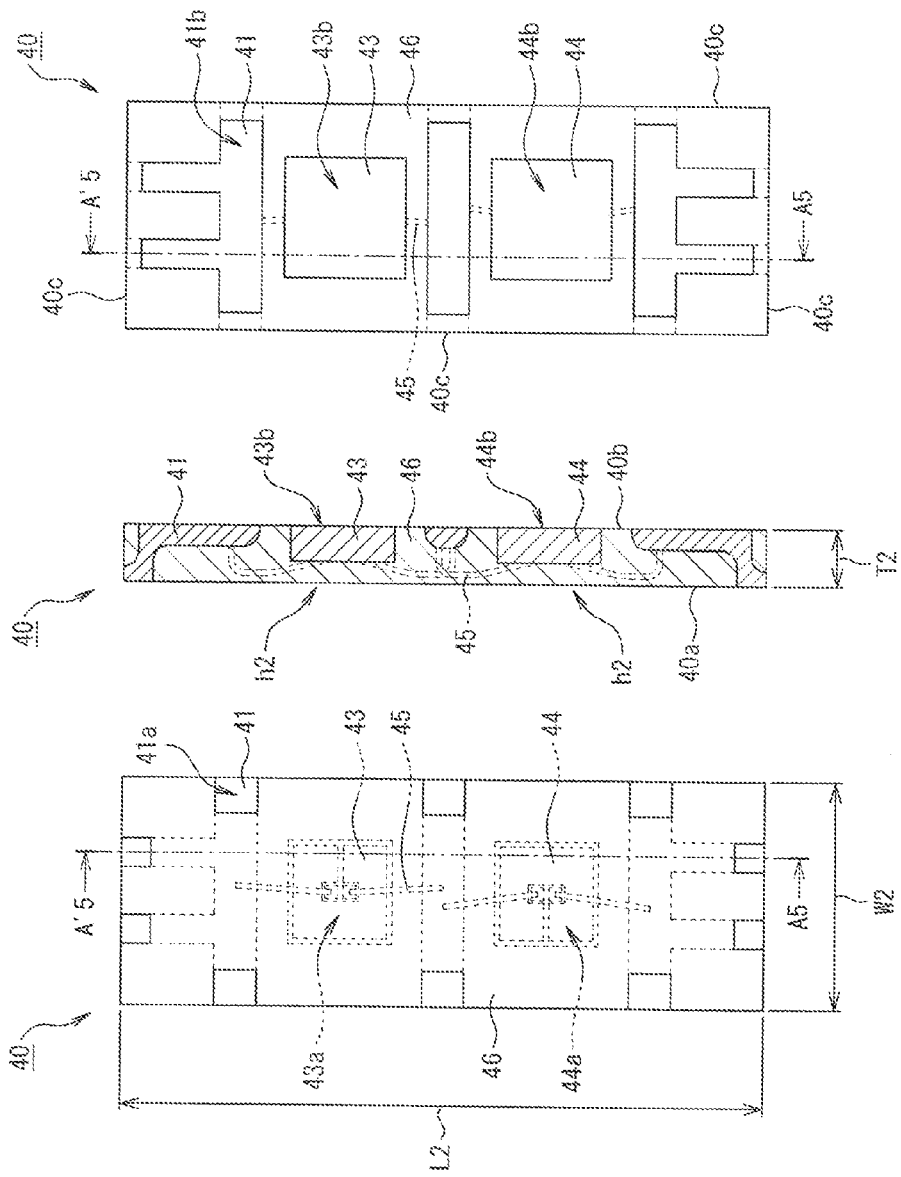

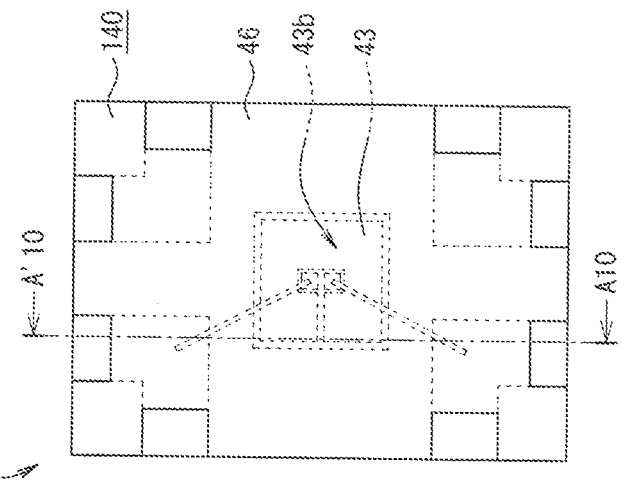
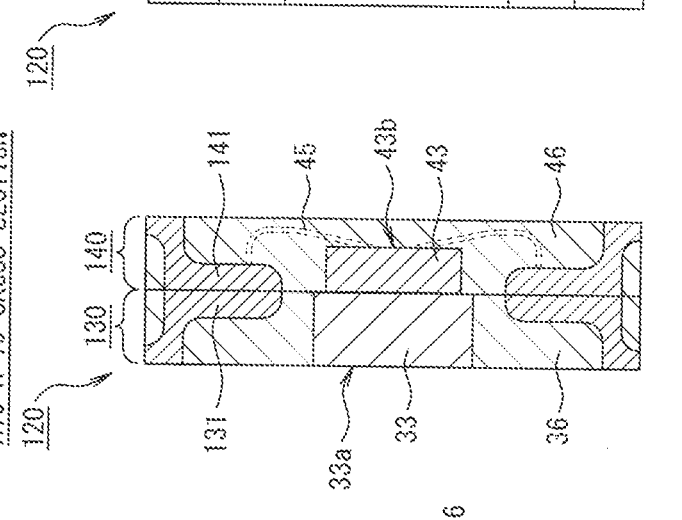
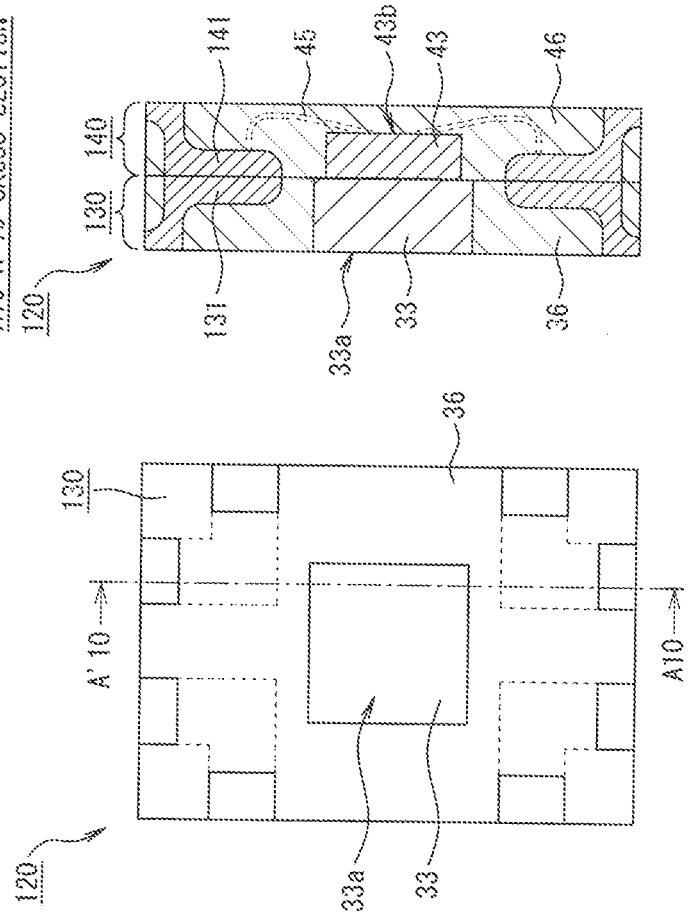

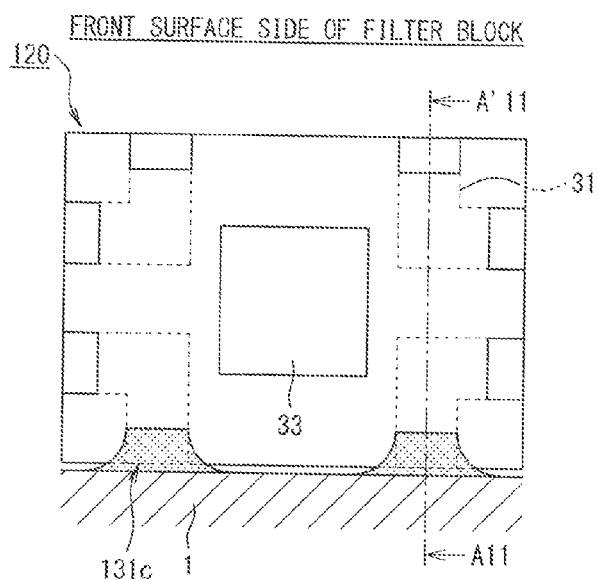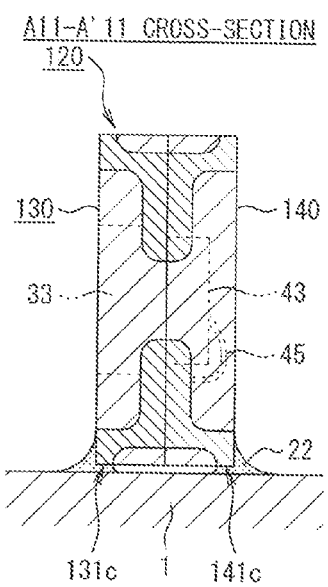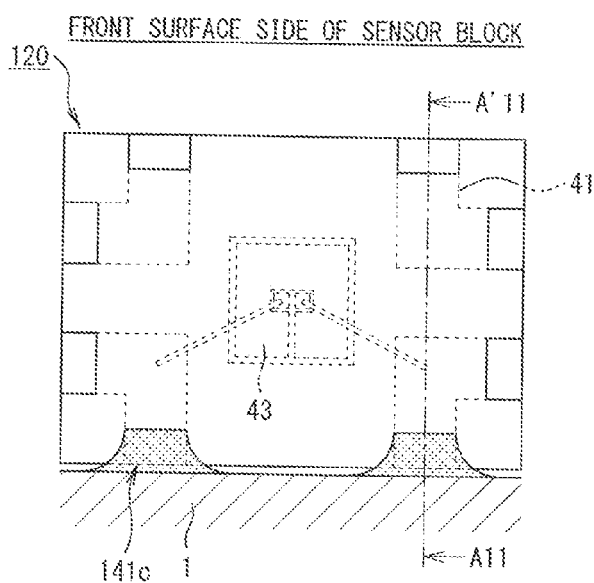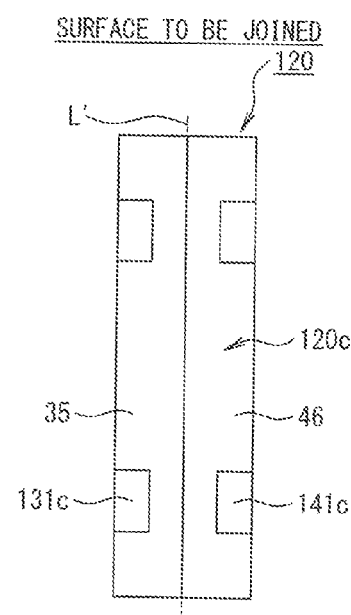

INFRARED SENSOR AND METHOD FOR MANUFACTURING SAME, FILTER MEMBER FOR INFRARED SENSOR, AND PHOTOCOUPLER

TECHNICAL FIELD

The present invention relates to an infrared sensor and a method for manufacturing the same, a filter member for an infrared sensor, and a photocoupler, and particularly to an infrared sensor capable of decreasing the size of the infrared sensor and a method for manufacturing the same, a filter member for an infrared sensor, and a photocoupler.

BACKGROUND ART

Patent Literature (PTL) 1 discloses examples of this kind of related art. In the publication, as illustrated in FIGS. 2A to 2C, an infrared sensor is disclosed which has a structure in which a sensor element equipped with an optical filter only transmitting infrared rays is covered with a resin except for the light-receiving surface. The sensor element is a quantum-type photodiode generating a photovoltaic effect using an infrared ray. In addition, the optical filter has a function of only transmitting an infrared ray having a specific wavelength.

CITATION LIST

Patent Literature

PTL 1: JP 2010-133946

SUMMARY OF INVENTION

Technical Problem

However, in a case in which an optical filter is mounted on a sensor element and the optical filter and the sensor element are disposed in a penetrating opening portion in a lead frame, thereby forming one package as disclosed in PTL 1, the opening portion in the lead frame is required to have a depth greater than the sum of the thickness of the sensor element, the thickness of the optical filter, and the loop height of a wire made of Au or the like. That is, when the thickness of a lead frame 190 (=the depth of an opening portion 191) is represented by T'1, the thickness of a sensor element 195 is represented by T'2, the thickness of an optical filter 196 is represented by T'3, and the loop height of a wire 197 electrically connecting the sensor element 195 and the lead frame 190 is represented by T'4 as illustrated in FIG. 12, T'1 is required to satisfy Expression (1) described below.

$$T'1 > T'2 + T'3 + T'4 \qquad (1)$$

However, an increase in the thickness of the lead frame 190 increases not only the depth T'1 of the opening portion 191 but also the width W of the opening portion 191 and thus there was a problem in that it was not possible to decrease the size of the infrared sensor.

In more detail, the penetrating opening portion 191 in the lead frame 190 as illustrated in FIG. 12 can be formed by, for example, etching the lead frame 190 from a front surface 190*a* and a rear surface 190*b*, respectively. This etching is isotropic wet etching in which the lead frame 190 is etched in the thickness direction (Z direction) and in the horizontal directions (X direction and Y direction) at the same time. Therefore, a larger thickness of the lead frame 190 brings about a larger width W of the opening portion 191 to be formed.

As another method for forming the opening portion 191, a method of punching the lead frame 190 using a mold can be considered; however, even in this method, it is not possible to form an opening portion having a smaller width W than the thickness T'1 of the lead frame 190.

The present invention has been made in consideration of the above-described circumstances, and an object of the present invention is to provide an infrared sensor capable of decreasing the size of the infrared sensor and a method for manufacturing the same, a filter member for an infrared sensor, and a photocoupler.

Solution to Problem

In order to solve the above-described problem, according to an aspect of the present invention, there is provided an infrared sensor including a filter member and a sensor member, in which the filter member includes a first lead terminal, an optical filter, and a first mold member configured to mold the first lead terminal and the optical filter, a light incidence surface and a light emission surface of the optical filter is exposed from the first mold member, the sensor member includes infrared sensor element, a second lead terminal electrically connected to the infrared sensor element, and a second mold member configured to mold the infrared sensor element and the second lead terminal, a light-receiving surfaces of the infrared sensor element are exposed from the second mold member, and the filter member is disposed on the sensor member such that the light emission surface of the optical filter faces the light-receiving surface of the infrared sensor element in the sensor member.

In the infrared sensor, the first lead terminal may be exposed from the first mold member and the second lead terminal may be exposed from the second mold member.

In the infrared sensor, when, out of side surfaces of the filter member, a side surface on a light emission surface side of the optical filter is defined as a first side surface, the first lead terminal may be exposed from the first mold member on the first side surface.

In the infrared sensor, when, out of side surfaces of the filter member, the side surface on the light emission surface side of the optical filter is defined as the first side surface, the first lead terminal may be exposed from the first mold member on a side surface opposite to the first side surface.

In the infrared sensor, when, out of the side surfaces of the filter member, the side surface on the light emission surface side of the optical filter is defined as the first side surface, the first lead terminal may be exposed from the first mold member on a side surface perpendicular to the first side surface.

In the infrared sensor, when, out of side surfaces of the sensor member, a side surface on a light-receiving surface side of the infrared sensor element is defined as a second side surface, the second lead terminal may be exposed from the second mold member on at least one side surface out of the second side surface, a side surface opposite to the second side surface, and a side surface perpendicular to the second side surface.

In the infrared sensor, the first lead terminal in the filter member may be exposed from the first mold member on the first side surface, the second lead terminal in the sensor member may be exposed from the second mold member on the second side surface, and the infrared sensor may further include a connection member configured to connect the first lead terminal exposed on the first side surface and the second lead terminal exposed on the second side surface.

In the infrared sensor, the connection member may be an insulating member.

In the infrared sensor, the connection member may be a conductive member.

The infrared sensor may include hollow portions between the filter member and the sensor member.

In the infrared sensor, in which the optical filter may be disposed between members constituting the first lead terminal, and the infrared sensor element may be disposed between members constituting the second lead terminal.

In the infrared sensor, the first lead terminal and the second lead terminal may have the same shape.

In the infrared sensor, the first lead terminal and the second lead terminal may be disposed at positions so as to face each other.

According to another aspect of the present invention, there is provided a method for manufacturing an infrared sensor including a filter member-forming step of forming a filter member including a first lead terminal, an optical filter, and a mold member configured to mold the first lead terminal and the optical filter, in which light incidence surfaces and a light emission surface of the optical filter is exposed from the first mold member; a sensor member-forming step of forming a sensor member including an infrared sensor element, a second lead terminal electrically connected to the infrared sensor element, and a second mold member configured to mold the infrared sensor element and the second lead terminal, in which a light-receiving surface of the infrared sensor element is exposed from the second mold member; and a disposition step of disposing the filter member on the sensor member so that the light emission surface of the optical filter in the filter member faces the light-receiving surface of the infrared sensor element in the sensor member.

In the method for manufacturing an infrared sensor, the filter member-forming step may include an optical filter-disposing step of disposing the optical filter in a first opening in the first lead frame including the first lead terminal; a step of sandwiching the first lead frame and the optical filter using a first mold; a step of loading the first mold member between the first lead frame and the optical filter sandwiched using the first mold and molding the first lead frame and the optical filter; and a taking-out step of taking out the first mold from the first lead frame, the optical filter, and the first mold member.

In the method for manufacturing an infrared sensor, the optical filter-disposing step may include a step of disposing the first lead frame on a surface including a gluing layer of a base material, and the taking-out step may include a step of peeling the base material off from the first lead frame.

In the method for manufacturing an infrared sensor, the filter member-forming step may include a step of forming filter members individualized by cutting a filter member including the first lead frame and the optical filter molded therein.

In the method for manufacturing an infrared sensor, the sensor member-forming step may include a step of disposing the infrared sensor element in second openings in the second lead frame including the second lead terminal; a step of electrically connecting the infrared sensor element to the second lead terminal; a step of sandwiching the second lead frame and the infrared sensor element using a second mold; a step of loading the second mold member between the second lead frame and the infrared sensor element sandwiched using the second mold and molding the second lead frame and the infrared sensor element; and a step of taking out the second mold from the second lead frame, the infrared sensor element, and the second mold member.

In the method for manufacturing an infrared sensor, the first lead frame and the second lead frame may have the same shape.

In the method for manufacturing an infrared sensor, the filter member-forming step may be a step of forming a filter member including a first lead terminal, an optical filter, and a first mold member configured to mold the first lead terminal and the optical filter, in which, when, out of side surface of the filter member, a side surface on a light emission surface side of the optical filter is defined as a first side surface, the first lead terminal is exposed from the first mold member on at least one side surface out of the first side surface, a side surface opposite to the first side surface, and a side surface perpendicular to the first side surface.

In the method for manufacturing an infrared sensor, the sensor member-forming step may be a step of forming a sensor member including a second lead terminal, an infrared sensor element, and a second mold member configured to mold the second lead terminal and the infrared sensor element, in which, when, out of side surfaces of the sensor member, a side surface on a light-receiving surface side of the infrared sensor element is defined as a second side surface, the second lead terminal is exposed from the second mold member on at least one side surface out of the second side surface, a side surface opposite to the second side surface, and a side surface perpendicular to the second side surface.

In the method for manufacturing an infrared sensor, in the filter member-forming step, the first lead terminal may be exposed on the first side surface, in the sensor member-forming step, the second lead terminal may be exposed on the second side surface, and the disposing step may include a step of connecting the first lead terminal exposed on the first side surface of the filter member and the second lead terminal exposed on the second side surface of the sensor member using an adhesive or a gluing agent.

In the method for manufacturing an infrared sensor, the adhesive or the gluing agent may be an insulating adhesive or an insulating gluing agent.

In the method for manufacturing an infrared sensor, the adhesive or the gluing agent may be a conductive adhesive or a conductive gluing agent.

According to still another aspect of the present invention, there is provided a filter member for an infrared sensor, including a first lead terminal; an optical filter; and a mold member configured to mold the first lead terminal and the optical filter, in which a light incidence surface and a light emission surface of the optical filter is exposed from the first mold member.

In the filter member for an infrared sensor, when, out of side surfaces of the filter member, a side surface on a light emission surface side of the optical filter is defined as a first side surface, the first lead terminal may be exposed from the first mold member on at least one side surface out of the first side surface, a side surface opposite to the first side surface, and a side surface perpendicular to the first side surface.

According to still another aspect of the present invention, there is provided a photocoupler including the infrared sensor; and a light-emitting device disposed away from the infrared sensor, in which a light-emitting surface of the light-emitting device and the optical filter face each other.

Advantageous Effects of Invention

According to the aspects of the present invention, since a thick lead frame satisfying Expression (1) described above is used, it is not necessary to form deep opening portions allowing the disposition of both the optical filter and the infrared sensor element therein. For example, when the first opening portion for disposing the optical filter is formed in the first lead frame and the second opening portion for disposing the infrared sensor element is formed in the second lead frame, it is possible to respectively decrease the depths of the opening portions h1 and h2 and it is also possible to decrease the opening width in accordance with the depth. Therefore, it becomes possible to decrease the size of the infrared sensor compared with the related art.

BRIEF DESCRIPTION OF DRAWINGS

FIGS. 2A to 2C are views illustrating a constitutional example of an IR light-receiving device 20;

FIGS. 3A to 3C are views illustrating a constitutional example of a filter member 30;

FIGS. 4A to 4C are views illustrating a constitutional example of a first lead terminal 31;

FIGS. 5A to 5C are views illustrating a constitutional example of a sensor member 40;

FIGS. 10A to 10C are views illustrating a constitutional example of an IR light-receiving device 120 according to a second embodiment;

FIGS. 11A to 11D are views illustrating a constitutional example of a surface to be joined 120c of the IR light-receiving device 120;

DESCRIPTION OF EMBODIMENTS

Embodiments of the present invention will now be described with reference to the drawings. In the respective drawings illustrated below, in some cases, members having the same constitution will be given the same reference sign and description thereof will not be repeated.

<First Embodiment>

(1) Constitution of Photocoupler

Figure 1A:
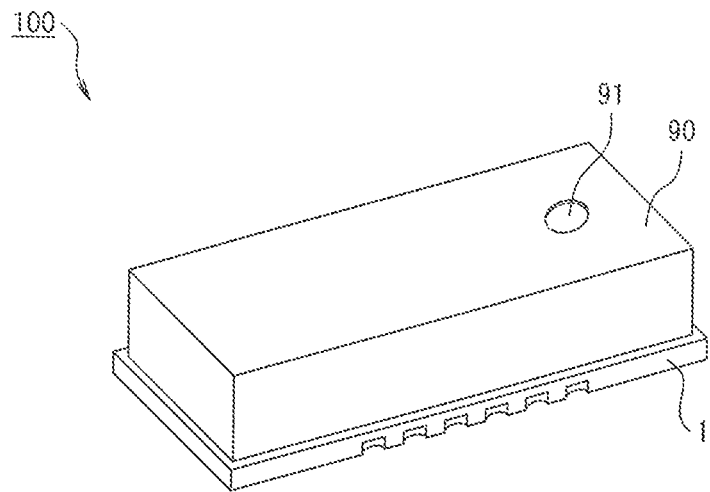
FIGS. 1A and 1B are views illustrating a constitutional example of a photocoupler 100 according to a first embodiment.
Figure 1B:
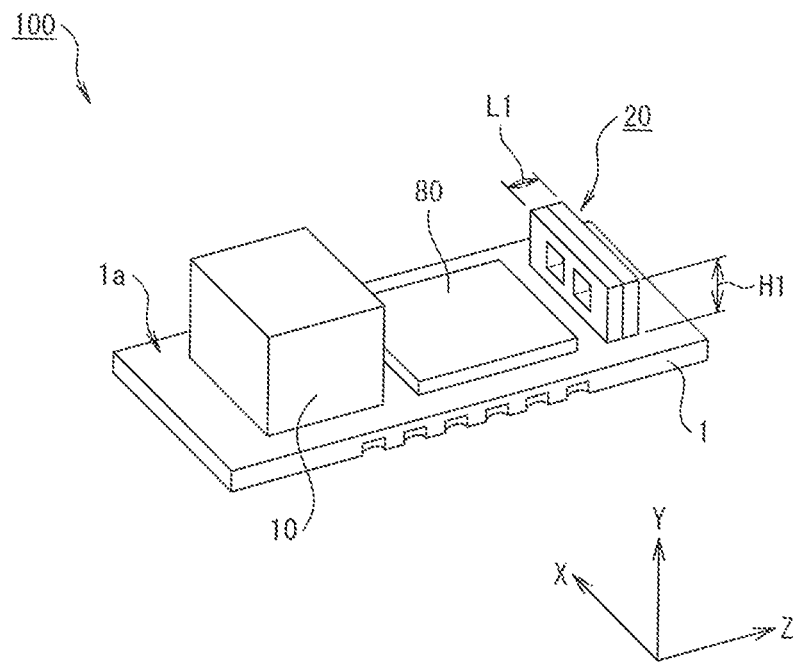

FIGS. 1A and 1B are perspective views illustrating constitutional examples of a photocoupler 100 according to a first embodiment of the present invention. It is to be noted that a state in which a chassis is taken out in order to illustrate a constitutional example of the inside of the photocoupler 100 is omitted in FIG. B.

As illustrated in FIGS. 1A and 1B, the photocoupler 100 includes, for example, an interconnection substrate 1, an infrared light-emitting device (hereinafter, the IR light-emitting device) 10 joined on a front surface 1a of the interconnection substrate 1, an infrared lighting-receiving device (hereinafter, the IR light-receiving device) 20 joined on the front surface 1a of the interconnection substrate 1 at a position away from the IR light-emitting device 10, a large-scale integrated circuit (hereinafter, the LSI) 80 which is disposed on the front surface 1a of the interconnection substrate 1 and carries out signal processes regarding the emitting and receiving of infrared light (for example, carries out the detection processes of gas and the like by outputting a control signal to the IR light-emitting device 10 and also obtaining an electric signal output from the IR light-receiving device), and a chassis 90 configured to enclose the IR light-emitting device 10, the IR light-receiving device 20, and the LSI 80 on the front surface 1a of the interconnection substrate 1 from the outside.

The IR light-emitting device 10 is a device configured to emit infrared light and examples thereof include an IR light-emitting diode and electric bulb (that is, the IR light-emitting device may be a device configured to emit only infrared light or a device configured to emit not only infrared light but also light having wavelengths other than the infrared light wavelength).

The IR light-receiving device 20 is a sensor device configured to receive infrared light and is a device configured to convert a received infrared ray to an electric signal and outputs the converted electric signal. In the photocoupler 100, a light-emitting surface of the IR light-emitting device 10 and a light-receiving surface (for example, a light incidence surface of a filter member described below) of the IR light-receiving device 20 face each other on the front surface 1a of the interconnection substrate 1. Therefore, an infrared light output from the IR light-emitting device 10 is incident on the light incidence surface of the filter member.

The chassis 90 is constituted using, for example, a light-blocking resin or metal and an opening portion 91 for gas inflow is provided in apart of the chassis. When enclosed by the light-blocking chassis 90, only light output from the light-emitting surface of the IR light-emitting device 10 is allowed to reach the light incidence surface of the filter member and other light (that is, light from the outside of the chassis) is not allowed to reach the light incidence surface. In the photocoupler 100, when the dimensional length of the IR light-receiving device 20 in a Z direction (that is, the thickness direction which is also a direction along a light path) is represented by L1 and the dimensional length of the IR light-receiving device 20 in a Y direction (that is, the height direction) is represented by H1, L1<H1 is satisfied and the IR light-receiving device 20 is a vertically-mounted device.

The vertically-mounted device refers to, in other words, a device in which the outline (package) is a cuboid, a first surface out of the six surfaces of the cuboid, which has the largest area, is orthogonal to the front surface 1a of the interconnection substrate 1, and a second surface, which is one of the six surfaces of the cuboid and has an area smaller than the first surface is joined to the front surface 1a of the interconnection substrate 1. In the present embodiment, the "second surface" is a surface to be joined 20c described below and a side surface of the lead terminal is exposed from the surface to be joined.

This exposed side surface is electrically connected to the interconnection substrate 1 (that is, vertically-mounted connection) as a plurality of terminal portions. Therefore, on the front surface 1a of the interconnection substrate 1, it is possible to reduce the mounting area (that is, foot print) of the IR light-receiving device 20.

(2) Constitution of IR Light-Receiving Device

FIGS. 2A to 2C are views illustrating a constitutional example of the IR light-receiving device 20. In detail, FIG. 2A is a front view of the IR light-receiving device 20, FIG. 2B is a cross-sectional view in the direction of A2-A'2, and FIG. 2C is a rear view of the IR light-receiving device 20.

As illustrated in FIGS. 2A to 2C, the IR light-receiving device (an example of the infrared sensor) 20 includes a filter member 30, a sensor member 40, and a connection member configured to connect the filter member 30 and the sensor member 40. The filter member 30 is disposed on the sensor member 40 so that the light emission surface of optical filters 33 and 34 face the light-receiving surfaces of infrared sensor elements 43 and 44 in the sensor member 40. The filter member 30 and the sensor member 40 are adhered to each other through the connection member on their rear surfaces. First, the filter member 30 will be described.

(2.1) Constitution of Filter Member

FIGS. 3A to 3C are views illustrating a constitutional example of the filter member 30. In detail, FIG. 3A is a front view of the filter member 30, FIG. 3B is a cross-sectional view in the direction of A3-A'3, and FIG. 3C is a rear view of the filter member 30.

As illustrated in FIGS. 3A to 3C, the filter member 30 includes a first lead terminal 31, two optical filters 33 and 34 disposed between parts of the first lead terminals 31 (that is, disposed between members constituting the first lead terminal 31), and a first mold member 35 configured to cover and mold the first lead terminal 31, the side surface of the optical filter 33, and the side surface of the optical filter 34. Regions between the parts of the first lead terminal 31 are defined as opening portions h1. The optical filters 33 and 34 are respectively disposed in the opening portions h1. In this example, light incidence surfaces 33a and 34a and light emission surfaces 33b and 34b of light of the optical filters 33 and 34 and part of the side surfaces of the first lead terminal 31 are respectively exposed from the first mold member 35.

FIGS. 4A to 4C are views illustrating a constitutional example of the first lead terminal 31. In detail, FIG. 4A is a front view of the first lead terminal 31, FIG. 4B is a cross-sectional view in the direction of A4-A'4, and FIG. 4C is a rear view of the first lead terminal 31.

As illustrated in FIGS. 4A to 4C, the first lead terminal 31 is formed by, for example, respectively selectively etching a copper (Cu) plate using a photolithography technique from their front surface 31a and rear surface 31b and plating the copper plate with nickel (Ni)-palladium (Pd)-gold (Au) or the like. The two penetrating opening portions h1 are respectively formed by, for example, etching the copper (Cu) plate from the front surface 31a and the rear surface 31b on both sides. The first lead terminal 31 includes regions etched halfway (half-etched regions) and regions not etched (non-etched regions) on each of the front surface 31a and the rear surface 31b. The half-etched regions are covered with the first mold member 35 and the non-etched regions are exposed from the first mold member 35. The thickness T1 (as described below, corresponding to the thickness of the filter member) of the non-etched section is, for example, 0.4 mm on either surface of the first lead terminal 31.

Back to FIGS. 3A to 3C, the optical filters 33 and 34 have a function of selectively transmitting light in a desired wavelength range (that is, the optical filters have high transmittance). For example, the optical filters 33 and 34 have a function of only transmitting infrared light. In addition, the optical filter 33 and the optical filter 34, for example, have different optical characteristics. For example, the optical filter 33 selectively transmits infrared light in a first wavelength range (long wavelength) and the optical filter 34 selectively transmits infrared light in a second wavelength range (short wavelength). Therefore, it becomes possible to specify the intensity and wavelength range of incident light on the basis of an electric signal output from the IR light-receiving element configured to receive infrared light through the optical filter 33 and an electric signal output from the IR light-receiving element configured to receive infrared light through the optical filter 34.

As a material of an optical member constituting the optical filters 33 and 34, a material configured to transmit predetermined infrared light such as silicon (Si), silica ($SiO_2$), sapphire ($Al_2O_3$), Ge, ZnS, ZnSe, $CaF_2$, and $BaF_2$ may be used. In addition, as a thin film material deposited to the optical member, silicon (Si), silica ($SiO_2$), sapphire ($Al_2O_3$), Ge, ZnS, $TiO_2$, $MgF_2$, $SiO_2$, $ZrO_2$, and $Ta_2O_5$ may be used. Furthermore, a dielectric multilayer film filter obtained by laminating dielectric bodies having different refractive indices on the optical member in a lamellar shape may be provided on both the front and rear surfaces with predetermined different thicknesses or may be provided on only one surface. In addition, in order to prevent unnecessary reflection, antireflection films may be formed on the outermost layers of either or both the front and rear surfaces.

The first mold member 35 is made of, for example, an epoxy-based thermosetting resin and is tolerant to a high temperature during reflow. The outline and size of the first mold member 35, that is, the package shape and size of the filter member 30 is, for example, a cuboid having a length L1, a width W1, and a thickness T1 of 4.5 mm, 1.15 mm, and 0.4 mm, respectively.

When, out of the side surfaces of the filter member 30, a side surface on a light emission surfaces 33b and 34b side of the optical filter is defined as a first side surface 30b and, out of the side surfaces of the filter member 30, the side surface of the filter member perpendicular to the first side surface 30b is defined as a third side surface 30c, and the first lead terminal 31 is respectively exposed from the first mold member 35 on the first side surface 30b, a side surface 30a on the side opposite to the first side surface 30b, and the third side surface 30c. Therefore, it becomes possible to respectively obtain communication or electric signals on the first side surface 30b, the side surface 30a on the side opposite to the first side surface, and the third side surface 30c.

The optical filters 33 and 34 are exposed from the first mold member 35 on the first side surface 30b and the side surface 30a, which is on the side opposite to the first side surface, of the filter member 30. Therefore, it is possible to prevent light having passed through the optical filters 33 and 34 from being absorbed by the first mold member 35.

(2.2) Constitution of Sensor Member

FIGS. 5A to 5C are views illustrating a constitutional example of the sensor member 40. In detail, FIG. 5A is a front view of the sensor member 40, FIG. 5B is a cross-sectional view in the direction of A5-A'5, and FIG. 5C is a rear view of the sensor member 40.

As illustrated in FIGS. 5A to 5C, the sensor member 40 includes a second lead terminal 41, two IR sensor elements 43 and 44 disposed between parts of the second lead terminals 41 (that is, disposed between members constituting the second lead terminal 41), a wire 45 which electrically connects the IR sensor elements 43 and 44 and the second lead terminal 41 and is made of gold (Au) or the like, and a second mold member 46 configured to cover the second lead terminal 41, the IR sensor elements 43 and 44, and the wire 45. Regions between the parts of the second lead terminal 41 are defined as opening portions h2. The IR sensor elements 43 and 44 are respectively disposed in the opening portions h2.

Light-receiving surfaces (that is, rear surfaces) 43b and 44b of the IR sensor elements 43 and 44, and part of the side surface and part of rear surface 41b of the second lead terminal 41 are respectively exposed from the second mold member 46. The front surfaces 43a and 44a of the IR sensor elements 43 and 44 are coated with the second mold member 46 and a front surface 41a of the second lead terminal 41 is exposed from the second mold member 46.

The second lead terminal 41 has the same shape and size as, for example, the first lead terminal 31 and is made of the same material as the first lead terminal. The second lead terminal 41 is also, similar to the first lead terminal 31, formed through selective etching using a photolithography technique and a plating treatment.

The IR sensor elements 43 and 44 are sensor elements detecting an infrared ray and include a light transmission substrate configured to transmit an infrared ray and a light-receiving unit formed on the front surface of the light transmission substrate. As the light transmission substrate, a GaAs substrate is used. In addition to the GaAs substrate, for example, substrates such as semiconductor substrates of Si, InAs, InP, GaP, Ge, and the like, GaN, AlN, sapphire substrates, and glass substrates may be used. When the above-described substrates are used as the light transmission substrate, it is possible to efficiently transmit light having a specific wavelength such as an infrared ray from the rear surfaces (that is, light-receiving surfaces) 43b and 44b of the IR sensor elements 43 and 44 toward the front surfaces 43a and 44a.

The second molding member 46 is made of, for example, an epoxy-based thermosetting resin and is tolerant to a high temperature during reflow. The outline and size of the second mold member 46, that is, the package shape and size of the sensor member 40 is, for example, the same as the filter member 30. For example, the package shape and size of the sensor member 40 is, for example, a cuboid having a length L2, a width W2, and a thickness T2 of 4.5 mm, 1.15 mm, and 0.4 mm, respectively.

The first mold member 35 and the second mold member 46 may be made of the same mold resin or different mold resins, but the first mold member 35 and the second mold member 46 are made of the same mold resin from the viewpoint of easy manufacturing.

When, out of the side surfaces of the sensor member 40, a side surface on a light-receiving surfaces 43b and 44b side of the IR sensor elements 43 and 44 is defined as a second side surface 40b and the side surface of the sensor member perpendicular to the second side surface 40b is defined as a fourth side surface 40c, the second lead terminal 41 is exposed from the second mold member 46 on the second side surface 40b, a side surface 40a on the side opposite to the second side surface 40b, and the fourth side surface 40c respectively. Therefore, it becomes possible to respectively obtain communication or electric signals from the second side surface 40b, the side surface 40a on the side opposite to the second side surface 40b, and the fourth side surface 40c.

The light-receiving surfaces of the IR sensor elements 43 and 44 are exposed from the second mold member 46 on the second side surface 40b of the sensor member 40. Therefore, it is possible to prevent light incident on the light-receiving surfaces of the IR sensor elements 43 and 44 from being absorbed by the second mold member 46.

(2.3) Connection Member

The connection member connects the first lead terminal 31 exposed from the first side surface of the filter member 30 and the second lead terminal 41 exposed from the second side surface of the sensor member 40. The first lead terminal 31 and the second lead terminal 41 are disposed at positions so as to face each other and are connected to each other through the connection member in the above-described state. The connection member is not particularly limited and the connection member may be an insulating gluing agent or an insulating adhesive or may be a conductive gluing agent or a conductive adhesive. The connection member may be, for example, insulating paste (for example, a thermosetting epoxy resin).

(2.4) Surface to be Joined of IR Light-Receiving Device

FIGS. 6A to 6D are views illustrating a constitutional example of a surface to be joined 20c in the IR light-receiving device 20. As illustrated in FIGS. 6A to 6D, in the IR light-receiving device 20, out of the four side surfaces, one side surface serves as the surface to be joined 20c joined onto the front surface 1a of the interconnection substrate 1.

Out of the side surfaces of the filter member 30, the side surface orthogonal to the joined surface between the filter member 30 and the sensor member 40 is defined as a side surface 31c. The first lead terminal 31 is exposed from the first mold member 35 on the side surface 31c of the filter member 30. Out of the side surfaces of the sensor member 40, the side surface orthogonal to the joined surface between the filter member 30 and the sensor member 40 is defined as a side surface 41c. The second lead terminal 41 is exposed from the second mold member 46 on the side surface 41c of the sensor member 40. In a state in which the filter member 30 and the sensor member 40 are attached together, the side surface 31c of the first lead terminal 31 and the side surface 41c of the second lead terminal 41 face the same direction and are disposed side by side on the surface to be joined 20c.

Therefore, the side surfaces 31c and 41c are joined to the interconnection substrate 1 through, for example, solder 22 and the surface 31a in contact with the side surface 31c and the surface 41a in contact with the side surface 41c function as a joining section in which the solder 22 is joined in a fillet shape (that is, a protruding state). In addition, the side surface 41c of the second lead terminal 41 is respectively electrically connected to the IR sensor elements 43 and 44 through the wire 45 and thus functions as a terminal portion for external connection.

The side surface 31c configured to function as a joining portion of the first lead terminal 31, the surface 31a in contact with the side surface 31c, the side surface 41c that is a joining portion of the second lead terminal 41 and also functions as the terminal portion for external connection, and the surface 41a in contact with the side surface 41c are disposed so as to be symmetric to each other with respect to the center line L of the surface to be joined 20c as an axis on both sides of the surface to be joined 20c. That is, regarding the shapes, sizes, and dispositions, the side surface 31c, the surface 31a in contact with the side surface 31c, the side surface 41c, and the surface 41a in contact with the side surface 41c are disposed so as to be horizontally symmetric to each other with respect to, for example, the center line L (that is, the boundary between the filter member 30 and the sensor member 40) of the surface to be joined 20c as an axis.

(3) Method for Manufacturing IR Light-Receiving Device

A step for manufacturing the IR light-receiving device 20 is classified into a step of manufacturing the filter member 30, a step of manufacturing the sensor member 40, and a disposition step for disposing the filter member 30 on the sensor member 40. The step of manufacturing the filter member 30 and the step of manufacturing the sensor member 40 may be carried out sequentially or in parallel. Herein, the step of manufacturing the filter member 30 will be described first, and then the step of manufacturing the sensor member 40 will be described. After that, the step of disposing both members will be described.

(3.1) Step of Manufacturing Filter Member

FIGS. 7A to 7E are process charts illustrating a method for manufacturing the filter member 30.

Figure 7A:
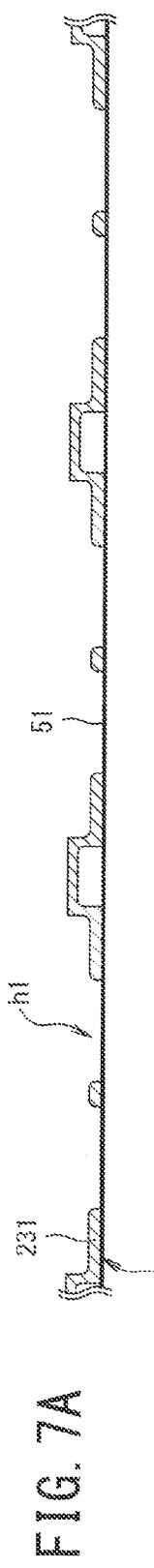
FIGS. 7A to 7E are views illustrating a method for manufacturing the filter member 30.

As illustrated in FIG. 7A, first, in the beginning, a heat-resistant gluing sheet 51 is prepared. Next, a rear surface 231b of a first lead frame 231 externally plated with Ni/Pd/Au is attached to a gluing layer of the gluing sheet 51. The first lead frame 231 is a thin metal plate including a section configured to serve as the first lead terminal 31 and the opening portions h1. The section in the first lead frame 231 which serves as the first lead terminal 31 is selectively etched from the front surface and the rear surface and is plated with nickel (Ni)-palladium (Pd)-gold (Au) or the like. The opening portions h1 are formed by respectively etching the front surface and rear surface of the first lead frame 231.

As the gluing sheet 51, heat-resistant gluing resin tape is used. In order to obtain better gluing properties, the thickness of the gluing layer is preferably thinner. In addition, in order to obtain better heat resistance, the gluing layer needs to be tolerant to a temperature in a range of approximately 150° C. to 200° C. As the above-described gluing sheet 51, for example, polyimide tape may be used. The polyimide tape is heat-resistant so as to be tolerant to approximately 280° C. The highly heat-resistant polyimide tape is also tolerant to high-temperature heat generated during the subsequent transfer molding or wire bonding.

As the gluing sheet 51, in addition to the polyimide tape, the following tape may be used.

- Polyester tape with a heatproof temperature of approximately 130° C. (the heatproof temperature may reach up to approximately 200° C. depending on the conditions of use)
- TEFLON (registered trademark) tape with a heat proof temperature of approximately 180° C.
- Polyphenylene sulfide (PPS) with a heat proof temperature of approximately 160° C.
- Glass cloth with a heat proof temperature of approximately 200° C.
- NOMEX paper with a heat proof temperature in a range of approximately 150 to 200° C.
- Additionally, aramid and crape paper may be used as the gluing sheet 51.

Figure 7B:
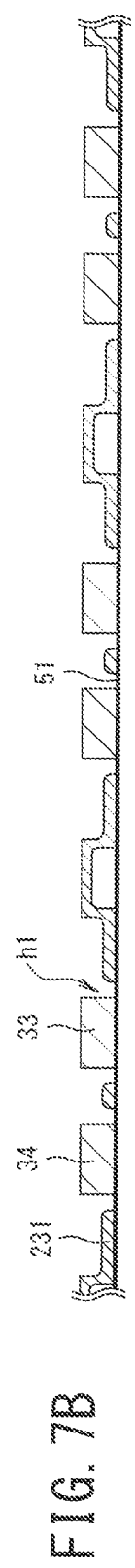

Next, as illustrated in FIG. 7B, the optical filters 33 and 34 are disposed in the penetrating opening portions h1 in the first lead frame 231 and, for example, the rear surfaces thereof (that is, the light emission surfaces) 33b and 34b are attached to the gluing layer of the gluing sheet 51. Meanwhile, protective films, not illustrated, may be attached to the front surfaces (that is, light incidence surfaces) 33a and 34a or rear surfaces (that is, light emission surfaces) 33b and 34b of the optical filters 33 and 34 in advance.

Figure 7C:
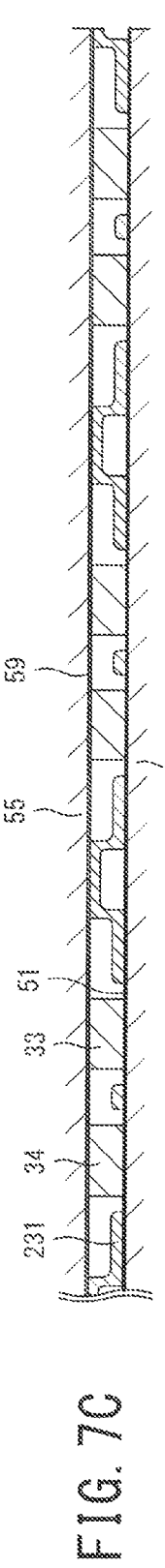

Next, as illustrated in FIG. 7C, an upper mold 55 is disposed on the front surface 231a of the first lead frame 231 and a lower mold 57 is disposed on the rear surface 231b of the first lead frame 231. The first lead frame 231 is sandwiched by the upper mold 55 and the lower mold 57, and a molten epoxy resin and the like are injected and loaded into the space sandwiched by the upper mold 55 and the lower mold 57 from the side. Therefore, the first mold member 35 is formed. That is, the first mold member 35 is loaded into a space between the first lead frame 231 and the optical filters 33 and 34 which are sandwiched by the upper mold 55 and the lower mold 57, and molds the first lead frame 231 and the optical filters 33 and 34.

In this step of forming the first mold member 35, in a state in which the regions not half-etched (that is, non-etched regions) on the front surface 231a of the first lead frame 231 and the upper mold 55 are in contact with each other through a fluororesin sheet 59 with no voids therebetween and the non-etched regions on the rear surface 231b of the first lead frame 231 and the lower mold 57 are in contact with each other through the gluing sheet 51 with no voids therebetween, the epoxy resin and the like are injected and loaded. Therefore, after the formation of the first mold member 35, the non-etched regions on the front surface 231a and rear surface 231b of the first lead frame 231 and the respective front surfaces 33a and 34a and respective rear surfaces 33b and 34b of the optical filters 33 and 34 are respectively in a state of being exposed from the first mold member 35.

Figure 7D:

Next, the upper mold 55 and the lower mold 57 are respectively moved upward and downward, whereby the first lead frame 231 including the first mold member 35 formed therein is taken out from both molds as illustrated in FIG. 7D. That is, the upper mold 55 and the lower mold 57 are taken out from the first lead frame 231, the optical filters 33 and 34, and the first mold member 35. In addition, the gluing sheet 51 is removed from the rear surface 231b of the first lead frame 231. After the removal of the gluing sheet 51, post curing for further curing the first mold member 35 and wet blasting necessary to completely remove thin burrs from the first mold member 35 are carried out and, furthermore, in a case in which the protective films, not illustrated, are formed on the front surfaces 33a and 34a or rear surfaces 33b and 34b of the optical filters 33 and 34, the protective films are removed. Therefore, a filter member 230 to which a plurality of the filter members 30 is connected is completed.

Figure 6A:
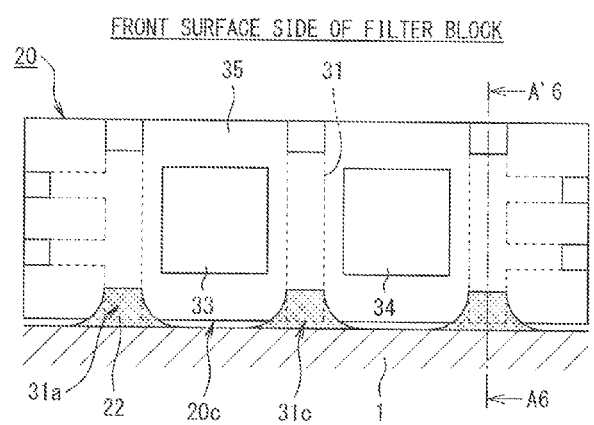
FIGS. 6A to 6D are views illustrating a constitutional example of a surface to be joined 20c of the IR light-receiving device 20.
Figure 6B:
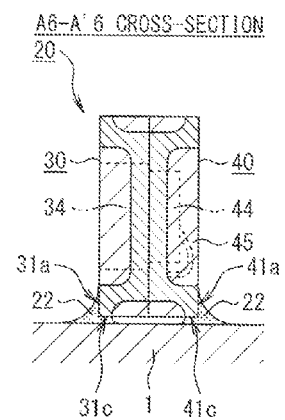
Figure 6C:
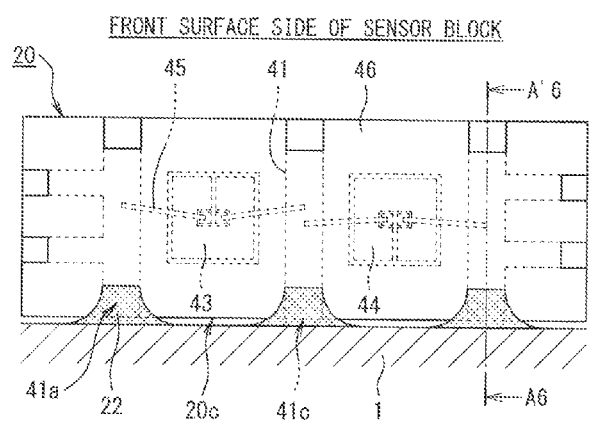
Figure 6D:
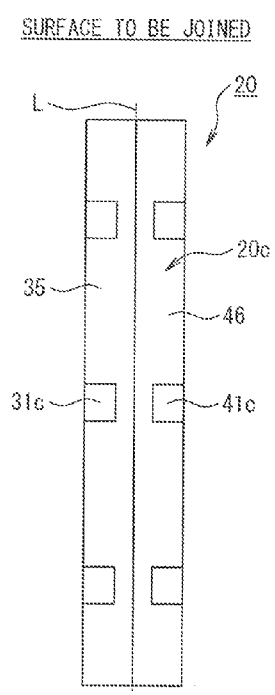
Figure 7E:
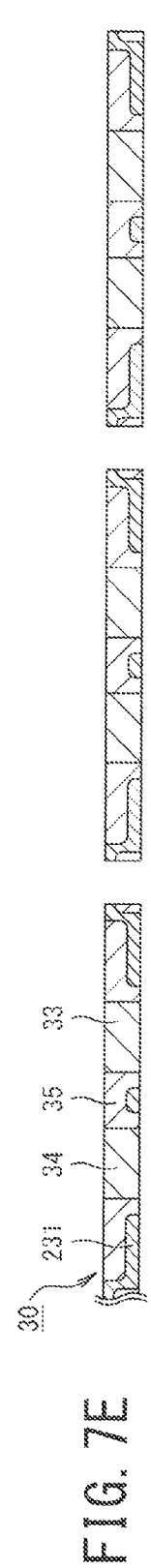

After that, the filter member 230 is attached to dicing tape, not illustrated, is diced using a dicing device, and is cut at a kerf width as illustrated in the drawing. Therefore, the filter member 230 is cut and separated into individual products as illustrated in FIG. 7E and individualized filter members 30 illustrated in FIG. 6B are completed.

(3.2) Step of Manufacturing Sensor Member

Figure 8A:
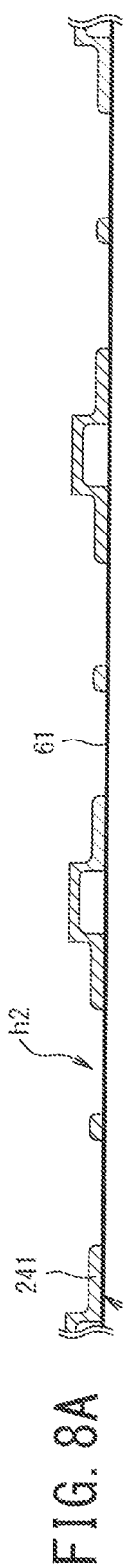
FIGS. 8A to 8F are views illustrating a method for manufacturing the sensor member 40.

FIGS. 8A to 8E are process charts illustrating a method for manufacturing the sensor member 40. As illustrated in FIG. 8A, first, in the beginning, a heat-resistant gluing sheet 61 is prepared. Next, a rear surface 241b of a second lead frame 241 externally plated with Ni/Pd/Au is attached to a gluing layer of the gluing sheet 61. The second lead frame 241 is a thin metal plate including a section configured to serve as the second lead terminal 41 and the opening portions h2. A section in the second lead frame 241 which serves as the second lead terminal 41 is selectively etched from the front surface and the rear surface and is plated with nickel (Ni)-palladium (Pd)-gold (Au) or the like. The opening portions h2 are formed by respectively etching the front surface and rear surface of the second lead frame 241. As the gluing sheet 61, it is possible to use the same tape as the gluing sheet 51.

Figure 8B:
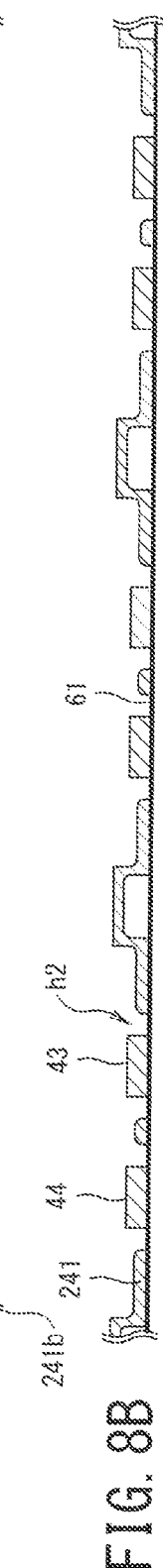

Next, as illustrated in FIG. 8B, the IR sensor elements 43 and 44 are disposed in the penetrating opening holes h2 in the second lead frame 241 and the rear surfaces (that is, the light-receiving surfaces) 43b and 44b of the IR sensor elements 43 and 44 are attached to the gluing layer of the gluing sheet 61.

Figure 8C:
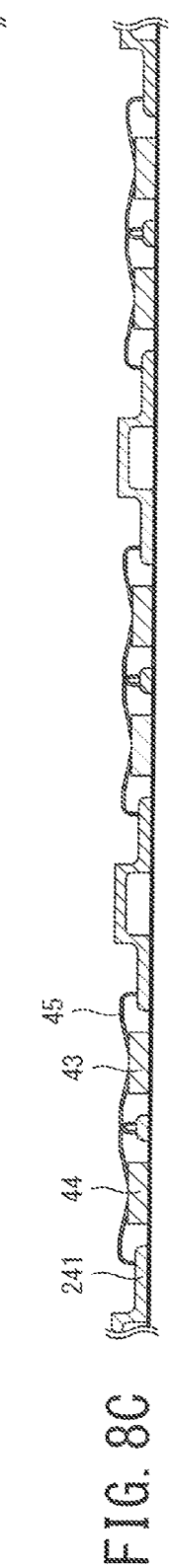

Next, as illustrated in FIG. 8C, the IR sensor elements 43 and 44 and the second lead frame 241 are electrically connected to each other using the wire 45. The IR sensor elements 43 and 44 and the second lead frame 241 are preferably electrically connected by extending the wire 45 from a terminal portion of the second lead frame 241 toward pad electrodes of the IR sensor elements 43 and 44 (that is, converse bonding when seen from the IR sensor elements 43 and 44). Since the terminal portion of the lead frame 41 is located lower than the pad electrodes of the IR sensor elements 43 and 44, it is possible to lower the height of the bonded wire 45.

Figure 8D:
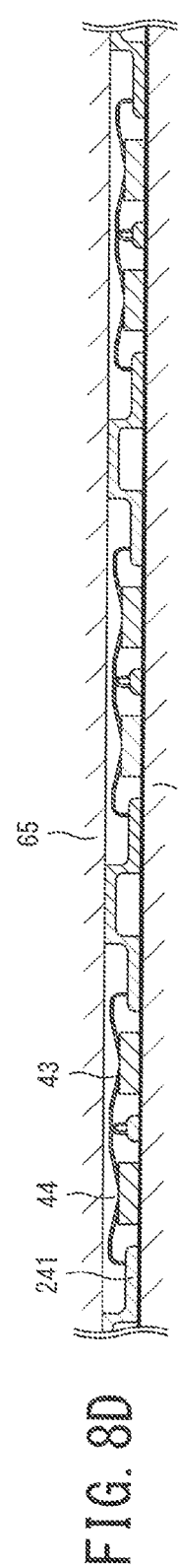

Next, as illustrated in FIG. 8D, an upper mold 65 is disposed on the front surface 241a of the second lead frame 241 and a lower mold 67 is disposed on the rear surface 241b of the second lead frame 241. The second lead frame 241 is sandwiched by the upper mold 65 and the lower mold 67, and a molten epoxy resin and the like are injected and loaded into the space sandwiched by the upper mold 65 and the lower mold 67 from the side. Therefore, the second mold member 46 is formed. As a material for the second mold member 46, it is possible to use the same material as the first mold member 35.

Figure 8E:
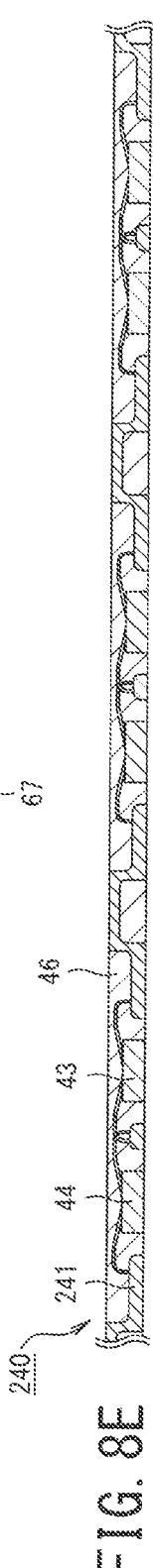

Next, the upper mold 65 and the lower mold 67 are respectively moved upward and downward, whereby the second lead frame 241 including the second mold member 46 formed therein is taken out from both molds as illustrated in FIG. 8E. In addition, the gluing sheet 61 is removed from the rear surface 241b of the second lead frame 241. After the removal of the gluing sheet 61, post curing for further curing the second mold member 46 and wet blasting necessary to completely remove thin burrs from the second mold member 46 are carried out. Therefore, a sensor member 240 to which a plurality of the sensor members 40 is connected is completed.

Figure 8F:
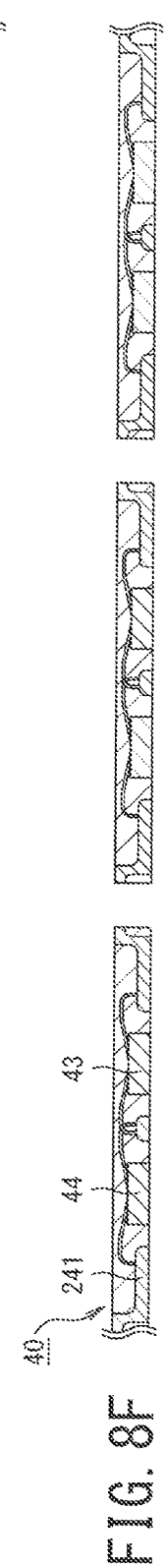

After that, the sensor member 240 is attached to dicing tape, is diced using a dicing device, and is cut at a kerf width as illustrated in the drawing. Therefore, the sensor member 240 is cut and separated into individual products as illustrated in FIG. 8F and individualized sensor members 40 illustrated in FIGS. 5A to 5C are completed.

(3.3) Disposing Step

Figure 9A:
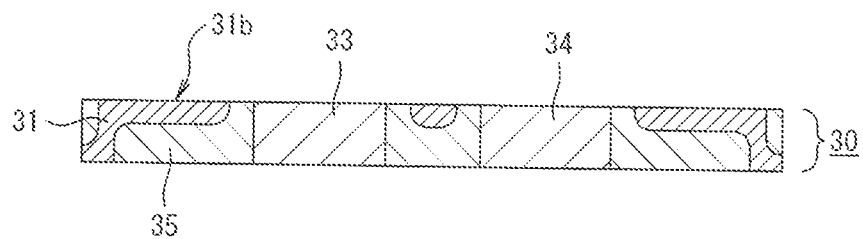
FIGS. 9A to 9C are views illustrating a method for attaching the filter member 30 and the sensor member 40.
Figure 9B:
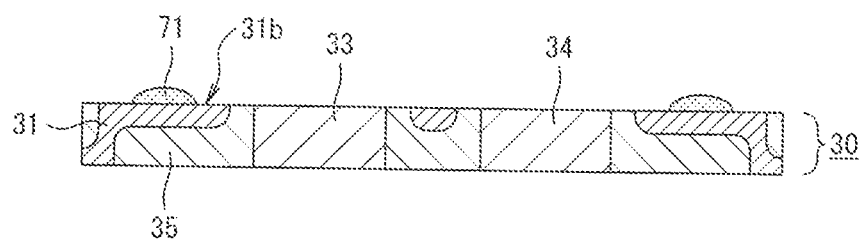
Figure 9C:
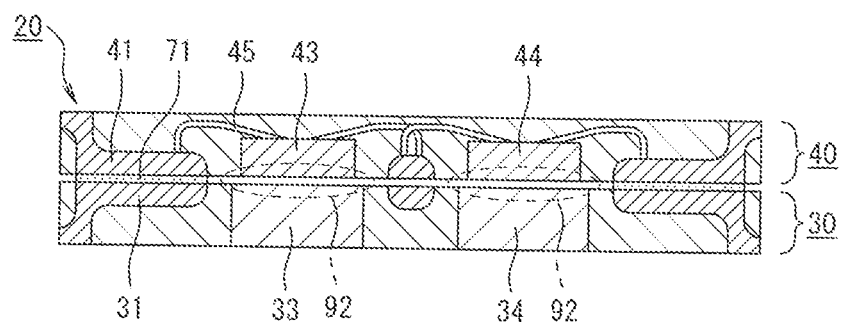
Figure 12:
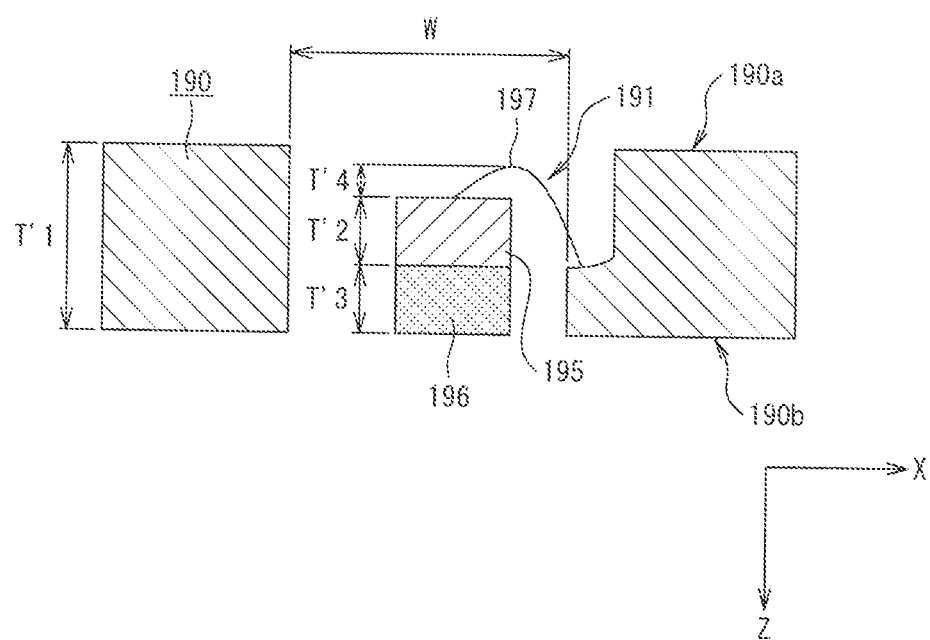
FIG. 12 is a view for describing a problem.

FIGS. 9A to 9C are process charts illustrating a method for attaching the filter member 30 and the sensor member 40 together. As illustrated in FIG. 9A, first, the filter member 30 is prepared. Next, as illustrated in FIG. 9B, the connection member is applied to the rear surface of the filter member 30. In the present embodiment, insulating paste 71 is used as the connection member. The insulating paste 71 may be applied to any regions other than the optical filters 33 and 34 and, for example, the insulating paste 71 is applied to the rear surface 31b of the first lead terminal 31 which is exposed from the first mold member 35. The insulating paste 71 is not applied onto the optical filters 33 and 34. The insulating paste 71 is, for example, an epoxy resin and is applied using a dispenser or a stamp.

Next, as illustrated in FIG. 9C, the rear surface of the sensor member 40 is brought into contact with the rear surface of the filter member 30 to which the insulating paste 71 has been applied and the insulating paste 71 is cured by carrying out, for example, a thermal treatment. The filter member 30 is attached to the sensor member 40 as described above, thereby completing the IR light-receiving device 20 illustrated in FIGS. 2A to 2C.

In the above description, the IR light-receiving device 20 (infrared sensor) is manufactured by connecting the individualized filter member 30 and the individualized sensor member 40 using the connection member such as the insulating paste 71; however, the IR light-receiving device 20 (infrared sensor) may be manufactured by connecting the filter member 230 to which a plurality of the filter members 30 is connected to the sensor member 240 to which a plurality of the sensor members 40 is connected using the connection member such as the insulating paste 71 and dicing the filter member 230 and the sensor member 240 connected to each other. The connection member may be a conductive adhesive. When a conductive adhesive is used as the connection member, it becomes possible to obtain an output signal of the infrared sensor element from the filter member side.

Since the IR light-receiving device 20 (infrared sensor) is formed by adhering the filter member 30 and the sensor member 40 together using the connection member, hollow portions 92 are present between the filter member 30 and the sensor member 40 in the IR light-receiving device 20. Hereinafter, the merits of the presence of the hollow portion 92 will be described.

In a case in which the connection member is applied to the filter member 30 or the sensor member 40, the connection member is preferably applied so that the air is not included in the connection member. However, there are cases in which the air is included in the connection member in a step of applying the connection member. When the connection member including the air is exposed to a high temperature, the air included in the connection member expands and thus there are cases in which the connection member is peeled off or the infrared sensor is broken. When the hollow portions 92, through which the air escapes, are present between the filter member 30 or the sensor member 40, the air included in the connection member escapes outside through the hollow portions 92 and thus the number of times of the peeling of the connection member or the breakage of the infrared sensor is extremely decreased.

In the first embodiment, the opening portions h1 correspond to first opening portions and the opening portions h2 correspond to second opening portions. The IR sensor elements 43 and 44 correspond to the infrared sensor elements and the wire 45 corresponds to a conductive member. In addition, the gluing sheet 51 corresponds to a base material. The upper mold 55 and the lower mold 57 correspond to a first mold and the upper mold 65 and the lower mold 67 correspond to a second mold. In addition, the IR light-receiving device 20 corresponds to the infrared sensor.

(4) Effects of First Embodiment

The first embodiment of the present invention exhibits the following effects.

(4.1) According to the photocoupler 100 illustrated in FIGS. 1A and 1B, it becomes possible to specify the intensity and wavelength range of incident light on the basis of an electric signal output from the IR light-receiving element 43 and an electric signal output from the IR sensor element 44. For example, for an infrared ray radiated in a specific gas atmosphere such as $CO_2$, a specific wavelength component is quantitatively absorbed depending on the type or concentration of the gas. Therefore, it is possible to detect the type and concentration of gas present in a light path by specifying the intensity and wavelength range of light which is radiated from the light-emitting device 10 and is incident on the IR light-receiving device 20. Therefore, the photocoupler 100 is extremely preferably available for a gas detector detecting a specific gas such as a $CO_2$ detector.

(4.2) Since the thick lead frame satisfying Expression (1) described above is used, it is not necessary to form deep opening portions allowing the disposition of both the optical filters and the IR sensor elements therein. When the opening portions h1 for disposing the optical filters 33 and 34 are formed in the first lead frame 231 and the opening portions h2 for disposing the IR sensor elements 43 and 44 are formed in the second lead frame 241, it is possible to decrease the depths of the opening portions h1 and h2 respectively and it is also possible to decrease the opening width in accordance with the depth. Therefore, it becomes possible to decrease the size of the IR light-receiving device compared with the related art.

(4.3) In a state in which the filter member 30 and the sensor member 40 are attached together, the side surface 31c of the first lead terminal 31 exposed from the first mold member 35 and the side surface 41c of the second lead terminal 41 exposed from the second mold member 46 face the same direction. Therefore, on the surface to be joined 20c of the IR light-receiving device 20, it is possible to respectively expose the side surfaces 31c and 41c and it is possible to respectively solder the side surfaces 31c and 41c to the front surface 1a of the interconnection substrate 1. That is, it is possible to use the respective side surfaces 31c and 41c of the first lead terminal 31 and the second lead terminal 41 as connection portions with respect to the interconnection substrate 1. Since the first lead terminal 31 and the second lead terminal 41 respectively include the connection portions, it is possible to increase the joining force between the IR light-receiving device 20 and the interconnection substrate 1 compared with a case in which only one of the first lead terminal 31 and the second lead terminal 41 includes the connection portion.

(4.4) The side surface 41c of the second lead terminal 41 is connected to the IR sensor elements 43 and 44 through the wire 45. Therefore, particularly, the side surface 41c is available not only as a simple connection portion but also as a terminal portion for external connection.

(4.5) The respective side surfaces 31c and 41c of the first lead terminals 31 and 41 are symmetrically disposed with respect to the boundary between the sensor member 40 and the filter member 30 as an axis. That is, on the surface to be joined 49, the side surfaces 31c and 41c are disposed in a horizontally symmetric manner with respect to the above-described boundary as an axis. Therefore, it becomes easy to maintain the balance of moment attributed to the properties and the like of the solder and it is possible to suppress, for example, the unidirectional leaning or collapsing of the IR light-receiving device 20 or the occurrence of the so-called Manhattan phenomenon.

(4.6) The first lead terminal 31 and the second lead terminal 41 have the same shape and the same size. Therefore, it is possible to dispose the first lead terminal 31 and the second lead terminal 41 completely symmetrically with respect to the boundary between the sensor member 40 and the filter member 30 as an axis. It becomes easy to maintain the balance of moment attributed to the properties and the like of the solder. In addition, it is possible to use only one type of lead frame to constitute the IR light-receiving device 20 and it becomes possible to use a common mold in forming the first mold member 35 and the second mold member 46. Therefore, it is possible to contribute to a decrease in the manufacturing cost of the IR light-receiving device 20.

(4.7) The first mold member 35 is formed using the upper mold 55 and the lower mold 57 (that is, using a transfer mold technique). Since the transfer mold technique is used, it is possible to accurately form the first mold member 35 in the previously-set shape and size. In addition, since the gluing sheet 51 and the fluororesin sheet 59 are used, it is possible to prevent the epoxy resin and the like from being attached to the light incidence surfaces 33a and 34a and the light emission surfaces 33b and 34b of the optical filters 33 and 34.

(4.8) Since it is possible to decrease the size of the IR light-receiving device 20, it also possible to decrease the size of the photocoupler 100.

(5) Modification Examples

In the first embodiment, a case in which the filter member 30 and the sensor member 40 are attached together using the insulating paste 71 has been described. However, in the present embodiment, conductive paste (for example, silver (Ag) paste) may be used instead of the insulating paste 71. In such a case as well, it is possible to adhere the rear surfaces of the filter member 30 and the sensor member 40 together. In addition, when a conductive adhesive such as the conductive paste is used, it becomes possible to obtain an output signal of the IR sensor elements 43 and 44 from the filter member 30 side.

<Second Embodiment>

In the first embodiment, a case in which the IR light-receiving device 20 includes the filter member 30 including two optical filters 33 and 34 and the sensor member 40 including two IR sensor elements 43 and 44 has been described. However, in the present invention, the number of the optical filters included in the filter member is not limited to two. The number of the optical filters included in the filter member may be one or three. Similarly, the number of the IR sensor elements included in the sensor member is also not limited to two. The number of the optical filters included in the sensor member may be one or three.

(1) Constitution of IR Light-Receiving Device

FIG. 10A to 10C are views illustrating a constitutional example of an IR light-receiving device 120 according to a second embodiment of the present invention. In detail, FIG. 10A is a front view of the IR light-receiving device 120, FIG. 10B is a cross-sectional view in the direction of A10-A' 10, and FIG. 10C is a rear view of the IR light-receiving device 120. As illustrated in FIGS. 10A to 10C, the IR light-receiving device 120 includes a filter member 130 and a sensor member 140. Although not illustrated in the drawing, the filter member 130 and the sensor member 140 are adhered to each other using, for example, an insulating adhesive on their rear surfaces.

The filter member 130 includes a first lead terminal 131, the optical filter 33 disposed between parts of the first lead terminals 131, and the first mold member 35 configured to cover the first lead terminal 131 and the respective side surface of the optical filter 33. The light incidence surface 33a and emission surface of the optical filter 33 and part of the side surfaces of the first lead terminal 131 are respectively exposed from the first mold member 35.

The sensor member 140 includes a second lead terminal 141, an IR sensor element 43 disposed between parts of the second lead terminals 141, the wire 45 configured to electrically connect the IR sensor element 43 and the second lead terminal 141, and a second mold member 46 configured to cover the second lead terminal 141, the IR sensor element 43, and the wire 45. The light-receiving surfaces (that is, the rear surfaces) of the IR sensor elements 43 and part of the side surface of the second lead terminal 141 are respectively exposed from the second mold member 46.

FIGS. 11A to 11D are views illustrating a constitutional example of a surface to be joined 120c in the IR light-receiving device 120. As illustrated in FIGS. 11A to 11D, in the IR light-receiving device 120 as well, out of the four side surfaces, one side surface serves as the surface to be joined 120c joined onto the front surface 1a of the interconnection substrate 1.

For example, the first lead terminal 131 constituting the filter member 130 includes a side surface 131c exposed from the first mold member 35. The second lead terminal 141 constituting the sensor member 140 includes a side surface 141c exposed from the second mold member 46. In a state in which the filter member 130 and the sensor member 140 are attached together, the side surface 131c of the first lead terminal 131 and the side surface 141c of the second lead terminal 141 face the same direction and are disposed side by side on the surface to be joined 120c.

Therefore, the side surfaces 131c and 141c function as joining portions joined to the interconnection substrate 1 using, for example, the solder 22. In addition, the side surface 141c of the second lead terminal 141 is electrically connected to the IR sensor element 43 through the wire 45 and thus also functions as a terminal portion for external connection.

The side surface 131c configured to function as a joining portion of the first lead terminal 131 and the side surface 141c which is a joining portion of the second lead terminal 141 and also functions as a terminal portion for external connection are disposed so as to be symmetric to each other with respect to, for example, the center line L' of the surface to be joined 120c as an axis on both sides of the surface to be joined 120c. That is, regarding the shapes, sizes, and dispositions, the side surface 131c and the side surface 141c are disposed so as to be horizontally symmetric to each other with respect to, for example, the center line (that is, the boundary between the filter member 130 and the sensor member 140) L' of the surface to be joined 120c as an axis.

(2) Method for Manufacturing IR Light-Receiving Device

The method for manufacturing the IR light-receiving device 120 is the same as the method for manufacturing the IR light-receiving device 20 described in the first embodiment. In the second embodiment, the IR light-receiving device 120 corresponds to the infrared sensor.

(3) Effects of Second Embodiment

According to the second embodiment of the present invention, the same effects as the effects (4.2) to (4.8) of the first embodiment are exhibited. In addition, the IR light-receiving device 120 illustrated in FIGS. 10A to 10C is available in, for example, photocouplers, motion sensors, and the like.

(4) Modification Examples

In the second embodiment as well, the modification examples described in the first embodiment may be applied. That is, the filter member 130 and the sensor member 140 may be attached together using insulating paste or conductive paste.

<Others>

The present invention is not limited to the respective embodiments described above. The designs of the respective embodiments may be modified on the basis of the knowledge of a person skilled in the art and aspects obtained by modifying the embodiments are also included in the scope of the present invention.

REFERENCE SIGNS LIST 1 interconnection substrate
1a front surface (of interconnection substrate)
10 IR light-emitting device
20, 120 IR light-receiving device
20c, 120c surface to be joined (of IR light-receiving device)
22 solder
30, 130 filter member
30b first side surface of filter member
30c third side surface of filter member
31, 131 first lead terminal
41, 141 second lead terminal
231 first lead frame
241 second lead frame
31a, 41a front surface (of lead terminal)
31b, 41b rear surface (of lead terminal)
231a, 241a front surface (of lead terminal)
231b, 241b rear surface (of lead terminal)
31c, 41c, 131c, 141c side surface (of lead terminal)
33, 34 optical filter
33a, 34a front surface (of light incidence surface)
33b, 34b rear surface (of light emission surface)
35 first mold member
46 second mold member
40, 140 sensor member
40b second side surface of sensor member
40c fourth side surface of sensor member
43, 44 IR sensor element
43a, 44a front surface
43b, 44b rear surface (light-receiving surface)
45 wire
49 surface to be joined
51, 61 gluing sheet
55, 65 upper mold
57, 67 lower mold
59 fluororesin sheet
71 insulating paste
90 chassis
91 opening portion
100 photocoupler
230 filter member (to which a plurality of filter members is connected)
240 sensor member (to which a plurality of sensor members is connected)

The invention claimed is:

1. An infrared sensor comprising:
a filter member;
a connection member; and
a sensor member,
wherein the filter member includes
a first lead terminal,
an optical filter, and
a first mold member configured to mold to the first lead terminal and the optical filter,
a light incidence surface and a light emission surface of the optical filter are exposed from the first mold member,
the sensor member includes
an infrared sensor element,
a second lead terminal electrically connected to the infrared sensor element, and
a second mold member configured to mold to the infrared sensor element and the second lead terminal,
a light-receiving surface of the infrared sensor element is exposed from the second mold member,
the filter member is disposed on the sensor member, wherein the light emission surface of the optical filter faces the light-receiving surface of the infrared sensor element in the sensor member; and
the connection member is disposed between the filter member and the sensor member, and hollow portions are present between the filter member and the sensor member.

2. The infrared sensor according to claim 1, wherein the first lead terminal is exposed from the first mold member and the second lead terminal is exposed from the second mold member.

3. The infrared sensor according to claim 1, wherein, when, out of side surfaces of the filter member, a side surface on a light emission surface side of the optical filter is defined as a first side surface, the first lead terminal is exposed from the first mold member on the first side surface.

4. The infrared sensor according to claim 1, wherein, when, out of the side surfaces of the filter member, the side surface on the light emission surface side of the optical filter is defined as a first side surface, the first lead terminal is exposed from the first mold member on a side surface opposite to the first side surface.

5. The infrared sensor according to claim 1, wherein, when, out of the side surfaces of the filter member, the side surface on the light emission surface side of the optical filter is defined as a first side surface, the first lead terminal is exposed from the first mold member on a side surface perpendicular to the first side surface.

6. The infrared sensor according to claim 3, wherein, when, out of side surfaces of the sensor member, a side surface on a light-receiving surface side of the infrared sensor element is defined as a second side surface, the second lead terminal is exposed from the second mold member on at least one side surface out of the second side surface, a side surface opposite to the second side surface, and a side surface perpendicular to the second side surface.

7. The infrared sensor according to claim 6, wherein the first lead terminal in
the filter member is exposed from the first mold member on the first side surface,
the second lead terminal in the sensor member is exposed from the second mold member on the second side surface, and
the infrared sensor further comprises a connection member configured to connect the first lead terminal exposed on the first side surface and the second lead terminal exposed on the second side surface.

8. The infrared sensor according to claim 7, wherein the connection member is an insulating member.

9. The infrared sensor according to claim 7, wherein the connection member is a conductive member.

10. The infrared sensor according to claim 1, further comprising: hollow portions between the filter member and the sensor member.

11. The infrared sensor according to claim 1, wherein the optical filter is disposed between members constituting the first lead terminal, and
the infrared sensor element is disposed between members constituting the second lead terminal.

12. The infrared sensor according to claim 1, wherein the first lead terminal and the second lead terminal have the same shape.

13. The infrared sensor according to claim 1, wherein the first lead terminal and the second lead terminal are disposed at positions so as to face each other.

14. A method for manufacturing an infrared sensor, comprising:
a filter member-forming step of forming a filter member including a first lead terminal, an optical filter, and a mold member configured to mold to the first lead terminal and the optical filter, wherein a light incidence surface and a light emission surface of the optical filter are exposed from the first mold member;
a sensor member-forming step of forming a sensor member including an infrared sensor element, a second lead terminal electrically connected to the infrared sensor element, and a second mold member configured to mold to the infrared sensor element and the second lead terminal, wherein a light-receiving surface of the infrared sensor element is exposed from the second mold member;
a connection member forming step of applying a connection member to a rear surface of the filter member so that the connection member is disposed between the filter member and the sensor member, and hollow portions are present between the filter member and the sensor member; and
a disposition step of disposing the filter member on the sensor member so that the light emission surface of the optical filter in the filter member faces the light-receiving surface of the infrared sensor element in the sensor member.

15. The method for manufacturing an infrared sensor according to claim 14, wherein the filter member-forming step includes
an optical filter-disposing step of disposing the optical filter in a first opening in the first lead frame including the first lead terminal,
a step of sandwiching the first lead frame and the optical filter using a first mold,
a step of loading the first mold member between the first lead frame and the optical filter sandwiched using the first mold and molding the first lead frame and the optical filter, and
a taking-out step of taking out the first mold from the first lead frame, the optical filter, and the first mold member.

16. The method for manufacturing an infrared sensor according to claim 15, wherein the optical filter-disposing step includes a step of disposing the first lead frame on a surface including a gluing layer of a base material, and
the taking-out step includes a step of peeling the base material off from the first lead frame.

17. The method for manufacturing an infrared sensor according to claim 15, wherein the filter member-forming step includes a step of forming filter members individualized by cutting a filter member including the first lead frame and the optical filter molded therein.

18. The method for manufacturing an infrared sensor according to claim 15, wherein the sensor member-forming step includes
a step of disposing the infrared sensor element in a second opening in the second lead frame including the second lead terminal;
a step of electrically connecting the infrared sensor element to the second lead terminal;
a step of sandwiching the second lead frame and the infrared sensor element using a second mold;
a step of loading the second mold member between the second lead frame and the infrared sensor element sandwiched using the second mold and molding the second lead frame and the infrared sensor element; and
a step of taking out the second mold from the second lead frame, the infrared sensor element and the second mold member.

19. The method for manufacturing an infrared sensor according to claim 18, wherein the first lead frame and the second lead frame have the same shape.

20. The method for manufacturing an infrared sensor according to claim 14, wherein the filter member-forming step is a step of forming a filter member including a first lead terminal, an optical filter, and a first mold member configured to mold to the first lead terminal and the optical filter, wherein, when, out of side surfaces of the filter member, a side surface on a light emission surface side of the optical filter is defined as a first side surface, the first lead terminal is exposed from the first mold member on at least one side surface out of the first side surface, a side surface opposite to the first side surface, and a side surface perpendicular to the first side surface.

21. The method for manufacturing an infrared sensor according to claim 20, wherein the sensor member-forming step is a step of forming a sensor member including a second lead terminal, an infrared sensor element, and a second mold member configured to mold to the second lead terminal and the infrared sensor element, wherein, when, out of side surfaces of the sensor member, a side surface on a light-receiving surface side of the infrared sensor element is defined as a second side surface, the second lead terminal is exposed from the second mold member on at least one side surface out of the second side surface, a side surface opposite to the second side surface, and a side surface perpendicular to the second side surface.

22. The method for manufacturing an infrared sensor according to claim 21, wherein, in the filter member-forming step, the first lead terminal is exposed on the first side surface, in the sensor member-forming step, the second lead terminal is exposed on the second side surface, and the disposing step includes a step of connecting the first lead terminal exposed on the first side surface of the filter member and the second lead terminal exposed on the second side surface of the sensor member using an adhesive or a gluing agent.

23. The method for manufacturing an infrared sensor according to claim 22, wherein the adhesive or the gluing agent is an insulating adhesive or an insulating gluing agent.

24. The method for manufacturing an infrared sensor according to claim 22, wherein the adhesive or the gluing agent is a conductive adhesive or a conductive gluing agent.

25. A photocoupler comprising:
the infrared sensor according to claim 1; and
a light-emitting device disposed away from the infrared sensor,
wherein a light-emitting surface of the light-emitting device and the optical filter face each other.

* * * * *